(12) United States Patent
Smith et al.

(10) Patent No.: US 12,178,445 B2
(45) Date of Patent: Dec. 31, 2024

(54) REPOSITIONAL CLIP WITH EXTENSION

(71) Applicants: BOSTON SCIENTIFIC MEDICAL DEVICE LIMITED, Galway (IE); BOSTON SCIENTIFIC SCIMED, INC., Maple Grove, MN (US)

(72) Inventors: Paul Smith, Smithfield, RI (US); Deepak Kumar Sharma, Muzaffarnagar (IN); Rajivkumar Singh, Thane (IN); Arun Adhikarath Balan, Aluva (IN); Sharath Kumar G, Kanakapura (IN)

(73) Assignees: Boston Scientific Medical Device Limited, Galway (IE); Boston Scientific Scimed, Inc., Maple Grove, MN (US)

( * ) Notice: Subject to any disclaimer, the term of this patent is extended or adjusted under 35 U.S.C. 154(b) by 423 days.

(21) Appl. No.: 17/662,924

(22) Filed: May 11, 2022

(65) Prior Publication Data
US 2022/0378433 A1    Dec. 1, 2022

Related U.S. Application Data

(60) Provisional application No. 63/202,083, filed on May 26, 2021.

(51) Int. Cl.
*A61B 17/00* (2006.01)
*A61B 17/10* (2006.01)
(Continued)

(52) U.S. Cl.
CPC .......... *A61B 17/1285* (2013.01); *A61B 17/10* (2013.01); *A61B 17/122* (2013.01);
(Continued)

(58) Field of Classification Search
CPC ..... A61B 17/068; A61B 17/083; A61B 17/10; A61B 17/12013; A61B 17/122;
(Continued)

(56) References Cited

U.S. PATENT DOCUMENTS

2011/0190578 A1* 8/2011 Ho ..................... A61B 1/00089
                                                    600/104
2020/0397445 A1* 12/2020 Shikhman ............ A61B 17/083

FOREIGN PATENT DOCUMENTS

JP    2003513737 A    4/2003
WO   2022/094619     5/2022

* cited by examiner

*Primary Examiner* — Kelly J Bekker
*Assistant Examiner* — Lindsey R. Rivers
(74) *Attorney, Agent, or Firm* — Fay Kaplun & Marcin, LLP (57) ABSTRACT

A clipping system includes an adapter mounted on an insertion device and a clip including first and second jaws connected via hinges so that the first and second jaws are movable between an insertion configuration and an initial deployed configuration. A deployment member is configured to move the clip distally over and off of the adapter so that, as the clip leaves the adapter, the clip moves from the insertion configuration to the initial deployed configuration. An extending member is releasably coupled to the clip and movably connected to the adapter, and is configured to permit the withdrawal of the adapter away from the clip while the extending member remains coupled to the clip to place the system in a review configuration. The extending member is operable to retract the clip over the adapter, freeing the clip from tissue on which it had been clipped.

20 Claims, 5 Drawing Sheets

(51) Int. Cl.
*A61B 17/122* (2006.01)
*A61B 17/128* (2006.01)
(52) U.S. Cl.
CPC ............... *A61B 2017/00296* (2013.01); *A61B 2017/00486* (2013.01)
(58) Field of Classification Search
CPC ............ A61B 17/1227; A61B 17/1285; A61B 2017/00296; A61B 2017/00486; A61B 2017/12018; A61B 1/00087; A61B 1/00135; A61B 1/0014
See application file for complete search history.

REPOSITIONAL CLIP WITH EXTENSION

PRIORITY CLAIM

The present disclosure claims priority to U.S. Provisional Patent Application Ser. No. 63/202,083 filed May 26, 2021; the disclosure of which is incorporated herewith by reference.

FIELD present disclosure relates to endoscopic devices and, in particular, relates to endoscopic clipping devices for treating tissue.

BACKGROUND

Physicians have become more willing to perform aggressive interventional and therapeutic endoscopic gastrointestinal (GI) procedures, which may increase the risk of perforating the wall of the GI tract or may require closure of the GI tract wall as part of the procedure. Such procedures may include, for example, the removal of large lesions, tunneling under the mucosal layer of the GI tract to treat issues below the mucosa, full thickness removal of tissue, treatment of issues on other organs by passing outside of the GI tract, and endoscopic treatment/repair of post-surgical issues (e.g., post-surgical leaks, breakdown of surgical staple lines, and anastomotic leaks).

Currently, tissue may be treated via endoscopic closure devices including through-the scope clips or over-the-scope clips. Over-the-scope clips may be particularly useful for achieving closure of larger tissue defects. These endoscopic closure devices can save costs for the hospital and may provide benefits for the patient. In some cases, however, current endoscopic closure devices may be difficult to use, time consuming to position, or insufficient for certain perforations, conditions and anatomies. For example, current over-the-scope clips generally require launching of the clip from a position in which the clip itself is not visible to the operator. That is, prior to clipping the operator may view the target tissue to be clipped and, based on this visualization of the target tissue may determine that the distal end of the device and the clip are in a desired position relative to the target tissue. Based on the observation of the target tissue, the operator then deploys the clip without being able to see the clip itself until it is deployed. Once deployed, such current over-the scope clips are generally incapable of being repositioned.

SUMMARY

The present embodiments are directed to a clipping system comprising an adapter extending from a proximal end configured to be mounted on an insertion device to a distal end, the adapter including a clip including first and second jaws. The first jaw and second jaws are connected via first and second hinges so that the first and second jaws are movable between an insertion configuration, in which the first and second jaws are separated from one another and an initial deployed configuration in which the first and second jaws are drawn toward one another, the first and second jaws being biased toward the initial deployed configuration. A deployment member configured to move the clip distally over and off of the adapter so that, as the clip leaves the adapter, the clip moves from the insertion configuration to the initial deployed configuration. An extending member is releasably coupled to the clip and movably connected to the adapter, the extending member being configured to permit the withdrawal of the adapter proximally away from the clip while the extending member remains coupled to the clip to place the system in a review configuration in which the clip is separated from the adapter to enhance visual observation of the clip. The extending member is operable to retract the clip proximally over the adapter so that the clip is forced open as the clip is retracted over the adapter freeing the clip from on which it had been clipped.

In an embodiment, the first extending member may be releasably coupled to the first hinge so that, when the clip is observed to be in a desired position, the clip can be finally deployed from the system by separating the first extending member from the clip.

In an embodiment, the system may further comprise a second extending member releasably coupled to the second hinge of the clip and movably connected to the adapter, the second extending member being configured to remain coupled to the clip while the system is moved to the review configuration, the second extending member being operable to cooperate with the first extending member to retract the clip proximally over the adapter from one of the review and initial deployment configurations.

In an embodiment, a distal end of the first extending member may include a loop configured to be hooked to the first hinge.

In an embodiment, a distal end of the first extending member may be biased radially away from a longitudinal axis of the adapter so that, when the loop of the first extending member is released from the first hinge, the distal end of the first extending member springs laterally outward to disengage from the clip.

In an embodiment, the loop of the first extending member may be configured to engage the clip so that a distally directed force applied to the first extending member is transmitted to the clip to move the clip distally over and off of the adapter, the loop of the first extending member being configured so that, when the clip applies a proximally directed force of at least a predetermined magnitude to the first extending member, the loop of the first extending member slides off of the first hinge to disengage the clip from the first extending member.

In an embodiment, the system may further comprise a user interface coupled to a proximal end of the deployment element and a proximal end of the first extending member to control a movement of the clip between the open insertion configuration, the initial deployed configuration and the review configuration.

In an embodiment, the user interface may include a first knob connected to the proximal end of the deployment element and a second knob connected to a proximal end of the first extending member.

In an embodiment, the system may further comprise a first lumen extending proximally from the adapter to the user interface, the first extending member extending through the first lumen so that the first extending members is longitudinally movable relative to the first lumen.

In an embodiment, a distal portion of the adapter, over which the clip is configured to be mounted, may include a flat portion extending along an exterior surface thereof to reduce a friction between the clip and the adapter as the clip slides distally along the adapter toward a final deployed configuration.

The present embodiments are also directed to a clipping system for treating tissue, comprising an endoscope including a shaft extending longitudinally from a proximal end to a distal end, an adapter including a proximal portion mounted over the distal end of the shaft of the endoscope and a distal portion extending distally from the proximal portion, and clip including a pair of jaws. Each of the pair of jaws extends along a curve from a first end to a second end, first ends of the pair of jaws connected to one another via a first hinge and second ends of the pair of jaws connected to one another via a second hinge so that the pair of jaws are movable between an open insertion configuration, in which the pair of jaws are separated from one another, and a closed configuration, in which the pair of jaws are moved toward one another, the clip configured to be mounted over the distal portion of the adapter in the open insertion configuration. A deployment member is configured to move the clip distally relative to the adapter from the open insertion configuration to an initial deployed configuration by moving the clip distally off of the adapter so that the clip is moved toward the closed configuration. First and second extending members extend from proximal ends accessible to a user via a user interface at the proximal end of the shaft to distal ends releasably coupled to the clip, so that a distal movement of the extending member relative to the endoscope moves the clip distally away from the distal end of the adapter from the initial deployed configuration to a review configuration by a distance selected so that the clip is visible via the endoscope.

In an embodiment, the first extending member may be releasably coupled to the first hinge of the clip and the second extending member is releasably coupled to the second hinge of the clip.

In an embodiment, distal ends of each of the first and second extending members may be biased radially away from a longitudinal axis of the adapter so that, when the first and second extending member are coupled to the first and second hinges, the distal ends of the first and second extending members are restrained toward an engaging configuration, and, when the distal ends of the first and second extending members are disengaged from the first and second hinges, the distal ends of the first and second extending members revert to their biased configuration to release the clip therefrom in a final deployed configuration.

In an embodiment, the pair of jaws may be biased toward the closed configuration so that, when the clip is mounted over the adapter, an exterior surface of the adapter holds the pair of jaws toward the open configuration and, when the clip is moved toward the initial deployed configuration, the pair of jaws are permitted to revert to the biased closed configuration.

In an embodiment, the system may further comprise first and second lumens extending proximally from the adapter to the user interface, each of the first and second extending members extending through a corresponding one of the first and second lumens so that the extending members are longitudinally movable relative to the lumens, the first and second lumens extending along opposing sides of the shaft of the endoscope.

The present embodiments are also directed to a method for treating tissue. A clip is inserted to a target area in a body lumen via an endoscope, the clip mounted over a distal end of an endoscopic shaft, via an adapter, in an open insertion configuration in which jaws of the clip are separated from one another. A suction force is applied through a working channel of the endoscope so that tissue is drawn into a channel of the adapter and between jaws of the clip. The clip is moved from the open insertion configuration to an initial deployed configuration by pushing the clip distally off of the adapter so that the jaws revert to a biased closed configuration, in which the jaws extend toward one another to grip the tissue received therebetween. Extending members, distal ends of which are releasably coupled to the clip, are moved distally relative to the endoscopic shaft so that the clip is moved distally away from a distal end of the adapter toward a review configuration in which the clip is visible via the endoscope.

BRIEF DESCRIPTION

DETAILED DESCRIPTION

The present disclosure may be further understood with reference to the following description and the appended drawings, wherein like elements are referred to with the same reference numerals. The present disclosure relates to a clipping system and, in particular, relates to an over-the-scope endoscopic clipping system, in which an initial placement of a clip may be viewed and adjusted prior to a final deployment thereof. Exemplary embodiments of the present disclosure comprise a clip mountable over a distal end of an endoscope via an adapter and releasably coupled to extending members so that the clip may be moved between an insertion configuration, an initial deployed condition and a review configuration in which the clip can be viewed prior to being finally deployed.

In the insertion configuration, the clip is mounted over the adapter in a proximal position maintained in the insertion configuration ready to receive tissue between jaws thereof while the clip's position minimizes its occlusion of the field of view of the endoscopic vision system. The insertion configuration is configured to facilitate insertion of the endoscope to a target site adjacent to tissue to be clipped while the system allows the clip to be deployed and clipped over tissue in an initial deployed configuration. The device permits the endoscope to be withdrawn proximally away from the clip and the tissue over which it is clipped while the clip remains coupled to the device in a review configuration. As the endoscope is withdrawn proximally while the clip remains in place over the target tissue, the field of view of the vision system of the endoscope widens to show the clip and the tissue clipped thereby so that the operator can determine whether the position of the clip is desirable or in need of adjustment.

If the operator determines that the clip is positioned as desired, the clip is deployed and left in place clipped over the target tissue. If the operator determines that the position of the clip needs adjustment, the endoscope and the adapter coupled thereto are moved distally to a position adjacent to the clip. The clip is then drawn proximally over the adapter to reopen the clip which is drawn proximally over the distal end of the adapter forcing the clip to open against its natural bias as the clip slides proximally back over the adapter to return to the insertion configuration. After the clip has been removed from the tissue and returned to the insertion configuration, the operator can re-position the endoscope and device as desired, draw target tissue into the adapter (e.g., under suction or a grasper applied via a working channel of the endoscope) and once more deploy the clip from the adapter over the target tissue in the initial deployed position.

The endoscope is then withdrawn proximally once again as the clip remains coupled to the device so that the device moves again into the review configuration. The position of the clip and the clipped tissue are again observed and, this process may be repeated until the clip is positioned as desired. When the operator sees that the tissue over which the clip is closed is the desired portion of tissue, the clip may be deployed and released from the device and endoscope as described below. It will be understood by those of skill in the art that terms proximal and distal, as used herein, are intended to refer to a direction toward and away from, respectively, a user of the device.

As shown in FIGS. 1-11, a clipping system 100 for treating tissue defects and/or perforations according to an exemplary embodiment comprises a clip 102 configured to be mounted to an endoscope 104 via an adapter 108. The adapter 108 is mounted over a distal end 106 of an endoscopic shaft 124 of the endoscope 104 so that the clip 102 is movable between an insertion configuration (FIG. 3), in which the clip 102 is mounted over the adapter 108 with the jaws of the clip 102 separated from one another to receive tissue therebetween and an initial deployed configuration (FIGS. 4-5), in which the clip 102 is moved distally relative to the adapter 108 so that the jaws close to grip tissue that has been drawn into the adapter 108.

The clip 102 is releasably connected to extending members 110, which facilitate movement of the clip 102 between the initial deployed configuration and a review configuration (FIG. 6), in which the endoscope is withdrawn proximally as the extending members 110 are extended distally away from the endoscope so that the clip 102 remains tethered to the device as the distal end 106 of the endoscope 104 is withdrawn proximally. This widens the field of view of the endoscope vision system relative to the clip and the target tissue and allows for some movement of the endoscope 104 relative to the clip to enable more extensive observation of the placement and/or position of the clip 102 relative to the target tissue. As described below, if the user determines the position of the clip is incorrect or sub-optimal, the user may move the endoscope 104 distally to a position adjacent to the clip 102 and then retract the clip 102 proximally by withdrawing the extending members 110 proximally relative to the adapter 108 so that the clip 102 is drawn back over the distal end of the adapter 108 forcing the clip 102 open as it is slid proximally back over the adapter 108 to return to the insertion configuration.

Figure 7:
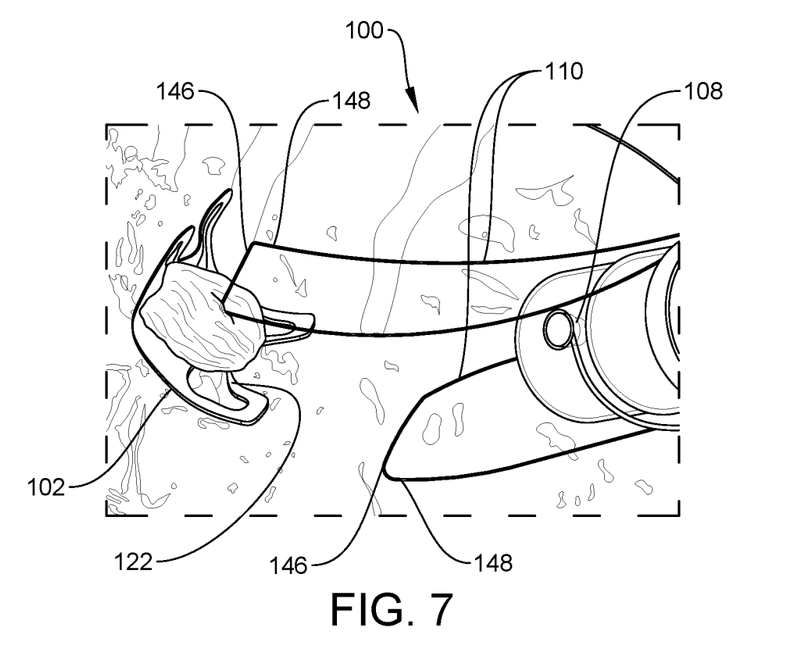
FIG. 7 shows a perspective view of the distal portion of the system of FIG. 1, in a final deployed configuration.

The user may then reposition the endoscope 104 and the clip 102 and repeat these steps so that the placement and/or position of the clip 102 relative to a target tissue may be adjusted prior to a final deployment of the clip 102, as shown in FIG. 7. That is, if the operator sees in the review configuration that the clip 102 is not positioned as desired, the clip 102 may be re-opened and removed from the tissue so that the device can be re-positioned until the clip 102 is closed over the desired portion of tissue. As will be described in further detail below, movement of the clip 102 between the insertion configuration, the initial deployed configuration, the review configuration and a final deployed configuration may be controlled via a user interface 112 which, in one embodiment, is coupled to a handle portion 114 at a proximal end 116 of the endoscopic shaft 124 of the endoscope 104.

The clip 102 includes a pair of jaws 118, each of the jaws 118 including gripping features 120 such as, for example, teeth, for gripping target tissue therebetween. The jaws 118 in this embodiment are connected to one another via hinges 122. In one embodiment, each of the jaws 118 extends along a curve from a first end 125 to a second end 127 so that a first one of the hinges 122 connects the first ends 125 of each of the jaws 118 to one another, while a second one of the hinges 122 connects the second ends 127 of each of the jaws 118 to one another. According to one exemplary embodiment, each the hinges 122 is a substantially C-shaped living hinge with a curve of the C-shape extending toward and between the jaws 118.

In one embodiment, the hinges 122 are spring biased, biasing the jaws 118 toward the initial deployed configuration in which the gripping features 120 of one of the jaws 118 contact the gripping features of the other jaw 118. In the initial deployed configuration, the jaws 118 extend toward one another so that target tissue may gripped between the jaws 118 via, for example, the gripping features 120. However, when the clip 102 is mounted over the adapter 108 in the insertion configuration, the jaws 118 extend about opposing portions of the adapter 108 so that an exterior surface 108 of the adapter 108 maintains the clip 102 open with the jaws 118 separated from one another so that target tissue may be received therebetween. When the clip 102 is moved distally off the adapter 108, the clip 102 is freed to close under the natural bias of the hinges 122. It will be understood by those of skill in the art that the hinges 122 and/or jaws 118 of the clips 102 may be formed of any of a variety of materials so long as the hinges 122 bias the jaws 118 toward the initial deployed configuration, as described above and so that the bias is sufficiently strong to maintain the clip 102 in position clipped over target tissue after the clip has been finally deployed. In one example, portions of the clip 102 (e.g., the hinges 122) are formed of a shape memory alloy such as, for example, Nitinol to provide and/or add to the bias toward the closed configuration.

As discussed above, in one embodiment the clip 102 is mounted to an endoscope 104 via an adapter 108. The adapter 108 is, in this embodiment, sized and shaped to be mounted on the distal end 106 of the endoscopic shaft 124 of a standard endoscope 104 although, as would be understood by those skilled in the art, the adapter 108 may be sized and shaped to be mounted over the distal end of any insertion device (flexible or rigid) suitable for accessing a target site within a body at which tissue to be clipped is located. The proximal end 116 of the endoscopic shaft 124 in this embodiment includes a handle portion 114 which may be used via a physician or other user, to guide the flexible endoscope through, for example, a bodily lumen (e.g., gastrointestinal tract) to a target site adjacent to target tissue to be clipped. As would be understood by those in the art, the endoscopic shaft 124 in this embodiment is sufficiently flexible to be inserted through even tortuous paths of the bodily lumen and thus, all of the components of this system that are extended through or along the endoscope to the clip 102 are also sufficiently flexible to permit this insertion to the target site.

The adapter 108 in this embodiment is a substantially tubular structure sized and shaped to be mounted over the distal end of an endoscope. The adapter 108 extends from a proximal end 126 to a distal end 128 and includes a channel 130 extending therethrough which, when the adapter 108 is mounted over the endoscope is substantially aligned with a longitudinal axis of the endoscope so that, when the adapter 108 is mounted on the distal end of the endoscope, the channel 130 extends away from the distal end of the endoscope so that occlusion of the field of view of the optical system of the endoscope is minimized. In one embodiment, the adapter 108 is substantially circular in cross-section to match a similar shape of the endoscope. As would be understood by those skilled in the art, however, if the endoscope is non-circular (e.g., oval) the adapter may be sized and shaped accordingly to provide, for example, a friction fit with the distal end of the endoscope.

A proximal portion 132 of the adapter 108 is configured to be mounted over the distal end 106 of the endoscopic shaft 124 while a distal portion 134 of the adapter 108 is configured to receive the clip 102 thereover and is sufficiently radially stiff to maintain the clip 102 in the open configuration against the bias of the hinges 122, as described above. In particular, since the jaws 118 of the clip 102 extend along curves, the clip 102 is mountable over the distal portion 134 so that each of the jaws 118 extends over a diametrically opposing portion of the adapter 108 with the jaws 118 held in the open configuration by an exterior surface 136 of the adapter 108.

Figure 8:
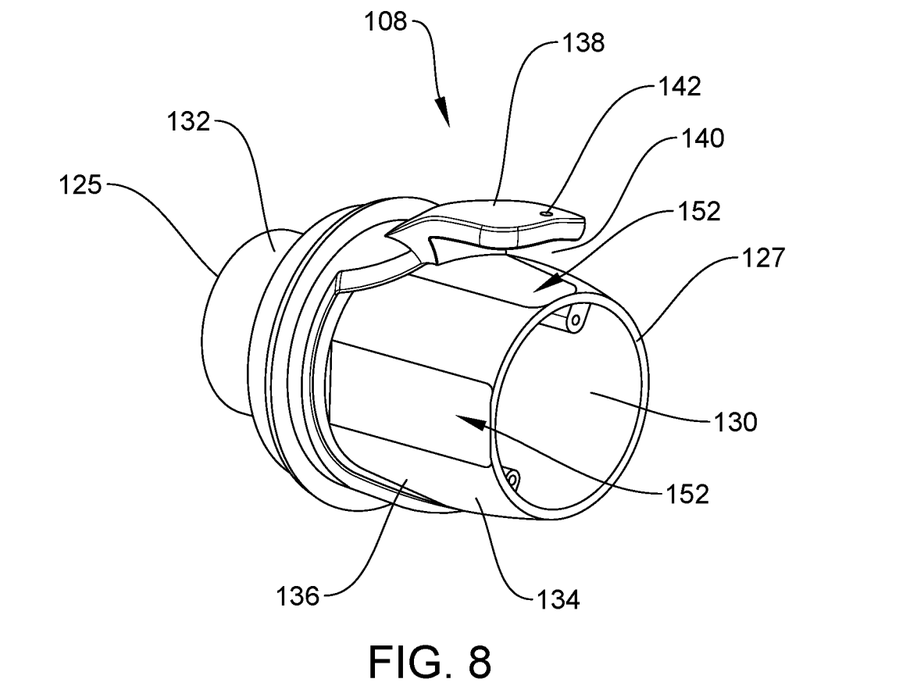
FIG. 8 shows a perspective view of an adapter according to the exemplary system of FIG. 1.
Figure 9:
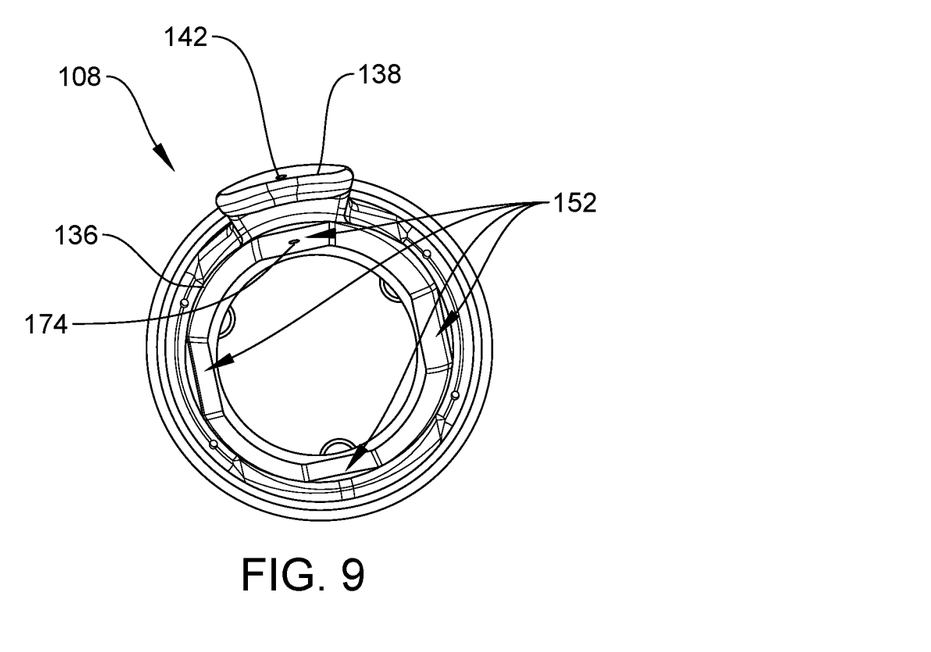
FIG. 9 shows a plan view of the adapter of FIG. 8.

As shown in FIGS. 8-9, the exterior surface 136 along the distal portion 134 of the adapter 108 of this embodiment includes a plurality of flat portions 152, each of which extends along all or a portion of a length of the distal portion 134 and about a portion of a perimeter (e.g., circumference) of the distal portion 134. In one embodiment, the exterior surface 136 includes four flat portions 152 extending along the distal portion 134, each of the flat portions 152 equally sized and separated from one another about the perimeter of the distal portion 134. It will be understood by those of skill in the art that these distal portions 152 are configured to reduce friction between the clip 102 and the adapter 108 to facilitate a movement of the clip 102 distally along the adapter 108 so that the clip 102 may be drawn distally over the adapter to deploy the clip 102 as desired and so that, if necessary, the clip 102 may be withdrawn proximally to reopen the clip 102 if the clip 102 needs to be re-positioned as will be described in further detail below. It will also be understood by those of skill in the art that although the adapter 108 is shown and described as including four equally spaced flat portions 152 along the exterior surface 136 of the distal portion 134, the adapter 108 may include any number of flat portions 152 along the distal portion 134 in any of a variety of configurations so long as the flat portions 152 facilitate the movement of the clip 102 proximally and distally along the distal portion 134 of the adapter 108.

The adapter 108 of this embodiment also includes a tab 138 extending from the exterior surface 136 of the adapter 108 toward the distal end 128 thereof so that a groove 140 is formed between the tab 138 and the exterior surface 136 along the distal portion 134. In the insertion configuration, the clip 102 of this embodiment is mounted over the distal portion 134 so that one of the jaws 118 is received within the groove 140. The tab 138 also includes a hole 142 extending therethrough, the hole 142 configured to receive a deployment element 144 such as, for example, a thread, strand, filament or other similar flexible longitudinal element used to move the clip 102 from the insertion configuration to the initial deployed configuration.

A first end of the deployment element 144 is releasably anchored (e.g., knotted) to the tab 138 via the hole 142 so that the deployment element 144 extends from the tab 138, across the groove 140 and through a working channel of the endoscope 104 via the channel 130 of the adapter 108 to a second end coupled to the user interface 112. In one embodiment, the deployment element 144 extends into the channel 130 via an opening of the channel 130 at the distal end 128 of the adapter 108. In another embodiment, the deployment element 144 extends into the channel 130 via a corresponding hole 174 extending through a wall of the distal portion 134 of the adapter 108. The corresponding hole 139 in this embodiment is coaxially aligned with the hole 142 extending through the tab 138, and is in communication with the channel 130.

In the insertion configuration, the deployment element 144 is slackened and extends across the groove 140 from the tab 138 to the working channel of the endoscope 104 proximally of the jaw 118. When it is desired to move the clip 102 from the insertion configuration to the initial deployed configuration, the user tensions the deployment element 144 so that the tensioned deployment element 144 draws the clip 102 distally to pull the clip 102 distally off of the adapter 108 to the initial deployed configuration. In the initial deployed configuration, the jaws of the clip 102 are closed and the clip 102 is positioned immediately distally of the distal end 128 of the adapter 108.

The movement of the clip 102 from the initial deployed configuration to the review configuration is achieved via the extending members 110. As will be described in further detail below, the extending member 110 also facilitate movement of the clip 102 from the review configuration back to the insertion configuration if, upon review of position of the clip 102 in the initial deployed configuration, it is desired to adjust a placement and/or position of the clip 102 relative to the target tissue. The extending members 110 extend from a distal end 148 releasably coupled to the clip 102 to a proximal end (not shown) coupled to the user interface 112. Each extending member 110 in this embodiment extends through, for example, a lumen 150 extending along a length of the endoscopic shaft 124 from the adapter 108 to the user interface 112 so that the extending member 110 is longitudinally movable relative to the lumen 150, and thereby the endoscopic shaft 124, to control movement of the clip 102 relative thereto.

In one embodiment, the system 100 includes two lumens 150 and two extending members 110, each of the lumens 150 being sized, shaped and configured to slidably accommodate a corresponding one of the extending members 110 therein. The lumens 150 in this embodiment extend along opposing longitudinal sides of the endoscopic shaft 124 so that positions of the lumens 150 are substantially aligned with the hinges 122 when the clip 102 is mounted over the adapter 108 in the insertion configuration. However, those skilled in the art will understand that any arrangement of the lumens 150 may be employed so long as the extending members 110 are slidably housed therein and are delivered to desired locations on the clip 102 as described above.

Each of the extending members 110 extends from the user interface 112 through a corresponding one of the lumens 150 so that its distal end 148 engages the clip 102 at a selected location. In an exemplary embodiment, the extending members 110 are formed as flexible strands, filaments or coils formed of, for example, a metal or polymer. In one exemplary embodiment, each extending member 110 is comprised of a flexible strand, filament or coil configured to form a loop 146 at the distal end 148 thereof for engaging the C-shaped hinge 122 of the clip 102. In this embodiment, each loop 146 is hooked over the C-shaped portion of a corresponding one of the hinges 122 and engages the corresponding hinge 122 (e.g., via a friction fit) so that, when the extending members 110 are extended distally relative to the adapter 108, the extending members 110 push the clip 102 distally over the adapter 108. In one embodiment, distal ends 148 of the extending members 110 are biased to deflect away from one another and away from a longitudinal axis of the adapter 108 and a longitudinal axis of the endoscope 104, toward a release configuration.

Those skilled in the art will understand that the loops of the extending members 110 are configured to engage the clip 102 so that, as the endoscope 104 and the adapter 108 are moved proximally away from a clip 102 that has been clipped to tissue, the clip 102 remains coupled to the device due to the connection of the loops over the hinges of the clip 102. The loops of the extending members 110 may be maintained in place on the clip 102 via, for example, a friction fit. The loops of the extending members 110 are configured so that, when the clip 102 applies a proximally directed force of at least a predetermined magnitude to the extending members 110 (e.g., when the extending members 110 are urged distally against the clip 102 while further distal movement of the clip 102 is prevented by the tissue to which it is clipped), the loops of the extending members 110 slide distally over and off of the hinges of the clip 102 to disengage the clip 102 from the extending members. This frees the clip 102 entirely from the system and permits the adapter 108, extending members 110 and the endoscope 104 to be withdrawn from the body as the clip 102 is left in place clipped on target tissue.

When the loops 146 are hooked over the C-shaped hinges 122, however, the distal ends 148 are restrained and pushed toward these longitudinal axes by the C-shaped hinges 122 in an engaged configuration. After the clip 102 has been clipped on target tissue and the adapter 108 and the clip 102 have been moved to the review configuration, the user can visually observe the position of the clip 102 on the tissue to determine if the clip 102 is in the desired position. If the user determines that the clip 102 is positioned as desired over the target tissue, the operator pushes the extending members 110 distally pressing the clip 102 into the target tissue. As the tissue provides resistance to further distal movement of the clip 102, the loops 146 are forced distally over the C-shaped hinges 122 until the distal ends of the loops 146 pass the distal ends of the hinges 122. At this point, the loops 146 are freed to spring radially outward away from the clip 102 de-coupling the clip 102 from the extending members 110 and from the device 100. That is, in the release configuration shown in FIG. 7, a distance between the distal ends 148 is greater than when the extending members 110 are restrained by the hinges 122 in the engaged configuration as the distal ends spring radially outward from the clip 102.

The lumens 150 may be fixed with respect to the endoscopic shaft 124 so that when the extending members 110 are longitudinally translated relative to the lumens 150, the extending members 110 move the clip 102 relative to the endoscope 104. In particular, the extending members 110 are formed of a material having a longitudinal stiffness sufficient so that, as the extending members 110 are moved distally with respect to the lumens 150, the clip 102 is pushed distally over the adapter 108 and when the extending members 110 are moved proximally with respect to the lumens 150, the clip 102 is drawn proximally with respect to the endoscope 104 over the adapter 108. In one embodiment, each of the lumens 150 includes a multi-lumen Bowden housing via which, for example, a strand of each extending member 110 is passed to create the loop 146 at the distal end 148.

Figure 10:
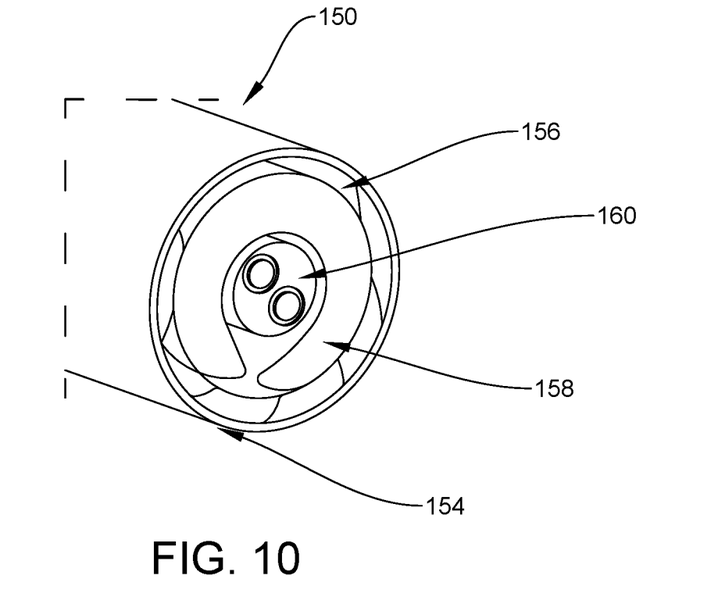
FIG. 10 shows a housing of a lumen according to the exemplary system of FIG. 1.

According to one embodiment, the Bowden housing, as shown in FIG. 10, includes an exterior plastic insulation 154, an interior braiding 156, a flexible coil therein 158, and a dual channel tube 160 extending longitudinally therethrough for accommodating portions of the extending member 110 to form the loop 146 at the distal end 148 of the extending member 110. The Bowden housing of the lumens 150 facilitate translational movement of the extending members 110 relative thereto while also preventing kinking of the extending members 110. Thus, to move the clip 102 from the initial deployed configuration to the review configuration, the extending members 110 are moved distally relative to the lumens 150 so that the endoscope 104 and the adapter 108 may be withdrawn proximally while the clip 102 remains coupled to the device and is positioned distally further from the distal end 127 of the adapter 108 and the distal end 106 of the endoscopic shaft 124. In this position, the clip 102 is more easily viewable via the optical system of the endoscope 104. If, upon review, it is desired to adjust a position/placement of the clip 102, the extending members 110 may be moved proximally with respect to the lumens 150 until the clip 102 is drawn proximally over the adapter 108 toward the insertion configuration.

As will be understood by those of skill in the art, a distally directed force applied by the distal end 128 of the adapter 108 against the jaws 118 as the clip 102 is drawn proximally will force the jaws 118 open against their natural bias. That is, as the clip 102 is drawn proximally over the adapter 108, the jaws 118 are pushed diametrically apart to slide over diametrically opposed portions of the adapter 108 as the clip 102 returns to the insertion configuration. The endoscope 104 and the adapter 108 may then be repositioned and, when the user feels the device is positioned as desired relative to target tissue to be clipped, the clip 102 may be moved, once again, to the initial deployed configuration and then to the review configuration, as described above, to confirm whether the clip 102 has been placed in a desired position relative to the target tissue.

According to one embodiment, when it is desired to release the clip 102 from the extending members 110 in a final deployed configuration, the extending members 110 may be moved distally relative to the clip 102 until the loops 146 are moved distally out of engagement with the hinges 122. In this embodiment, as the loops 146 are moved distally of the C-shaped hinges 122 and out of engagement therewith, the distal ends 148 of the extending members 110 are released from the hinges 122 and permitted to revert to their biased configuration, in which the distal ends 148 move radially away from one another. Since, at this point, the distal ends 148 extend radially away from one another and no longer engage the clip 102, as shown in FIG. 7, the clip 102 is fully separated from the device and the extending members 110 may be moved proximally away from the clip 102 without re-engaging the clip 102. Thus, the clip 102 may be left within the body clipped to target tissue while the endoscope 104 and the adapter 108 including the extending members 110 are withdrawn from the body.

It will be understood by those of skill in the art that although the clip 102 is described and shown as having C-shaped hinges 122, the hinges 122 may have any of a variety of shapes and configurations so long as the hinges 122 are configured to bias the jaws 118 of the clip 102 toward the closed configuration, as described above, and can be releasably engaged by the extending members 110. Similarly, it will be understood by those of skill in the art that the distal ends 148 of the extending members 110 may have any of a variety of shapes and configurations so long as the distal ends 148 are configured to releasably engage the hinges 122, as described above.

Figure 11:
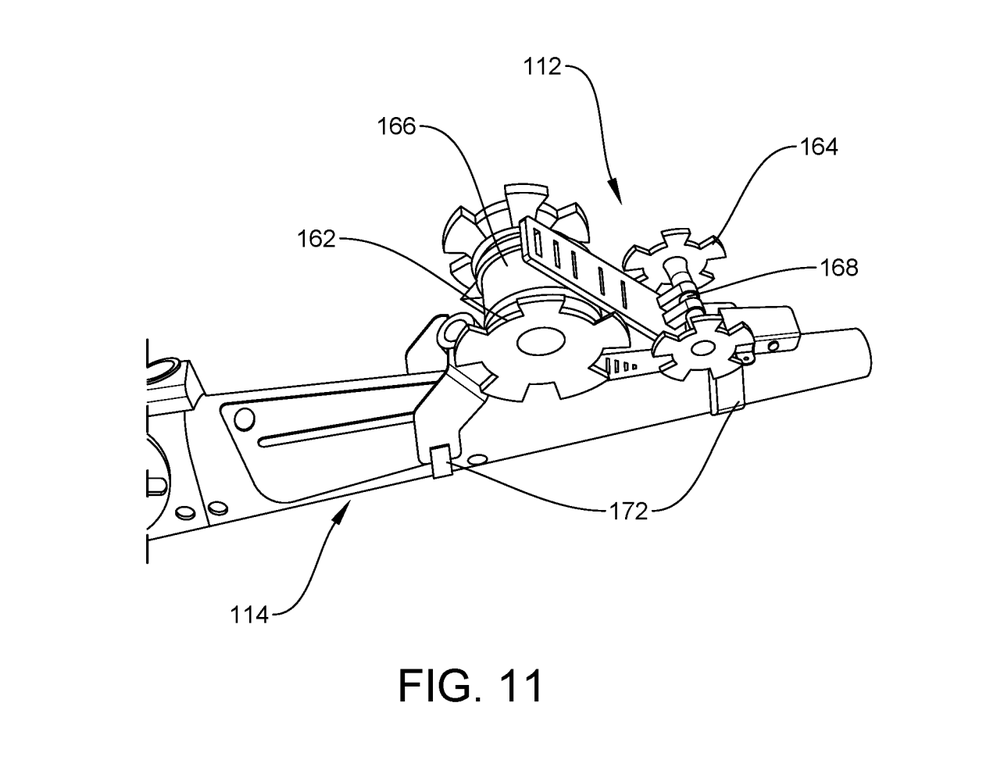
FIG. 11 shows a perspective view of a user interface according to the exemplary system of FIG. 1.

As described above, the user interface 112 may be used to actuate the deployment element 144 and the extending members 110. As shown in FIG. 11, the user interface 112 may be coupled to the handle portion 114 of the endoscope 102 via any of a number of coupling mechanisms including, for example, a snap interface 172. In one embodiment, the user interface 112 includes two actuating elements—e.g., a first knob 162 for controlling the deployment element 144 and a second knob 164 for controlling the extending members 110. The first and second knobs 162, 164 may be configured, for example, as thumb wheels so that the user of the system 100 may easily control a movement of the deployment element 144 and extending members 110 as they are holding the endoscope 104 via the handle 114.

As will be understood by those of skill in the art, a proximal end of the deployment element 144 may extend proximally from the working channel of the endoscopic shaft 124 to be wound around a first rotary wheel 166 that is connected to the first knob 162 so that a rotation of the first knob 162 correspondingly rotates the first rotary wheel 166, thereby moving the deployment element 144 as desired. For example, a rotation of the first knob 162 in a first direction may slacken the deployment element 144 when, for example, the clip 102 is mounted over the adapter 108 toward the insertion configuration. A rotation of the first knob 162 in a second direction opposite the first direction may tension the deployment element 144 when, for example, it is desired to move the clip 102 from the insertion configuration to the initial deployed configuration.

Similarly, the second knob 164 may be connected to a second rotary wheel 168 about which proximal ends of the extending members 110 may be wound so that a rotation of the second knob 164 controls a movement of the extending members 110, and thereby the clip 102. For example, proximal ends 170 of the lumens 150 may be connected to the user interface 112 so that proximal ends of the extending members 110 extend from the proximal ends 170 of the lumens 170 to be wound about the second rotary wheel 168. Thus, a rotation of the second knob 164 in a first direction may translate the extending members 110 distally with respect to the lumens 150 and endoscopic shaft 124 so that the clip 102 may be moved from the initial deployed configuration to the review configuration. Rotation of the second knob 164 in a second direction opposite the first direction will translate the extending members 110 in a proximally relative to the lumens 150 and the endoscopic shaft 124 so that the clip 102 may be drawn proximally from review configuration toward the insertion configuration to, for example, reposition the clip 102.

Figure 1:
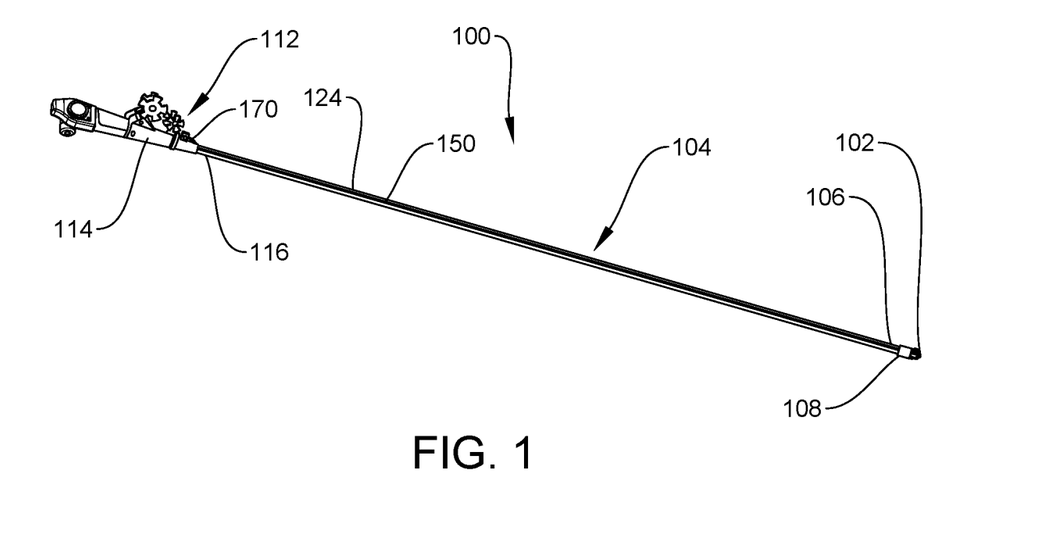
FIG. 1 shows a perspective view of a system according to an exemplary embodiment of the present disclosure.
Figure 2:
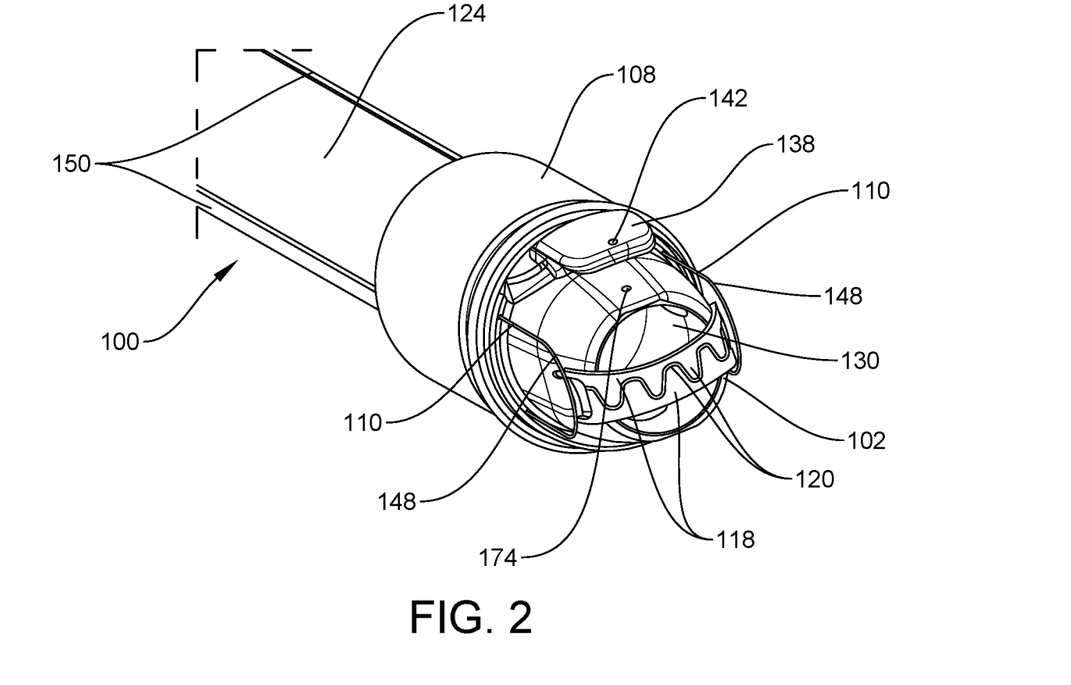
FIG. 2 shows a perspective view of a distal portion of the system of FIG. 1.
Figure 3:
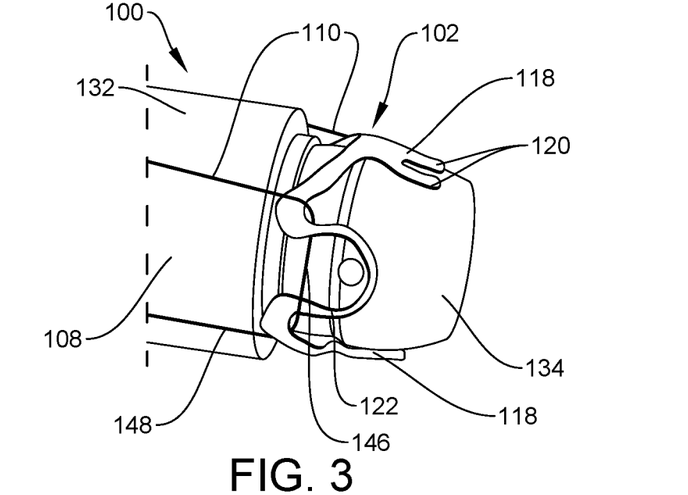
FIG. 3 shows a longitudinal side view of the distal portion of the system of FIG. 1, in an insertion configuration.
Figure 4:
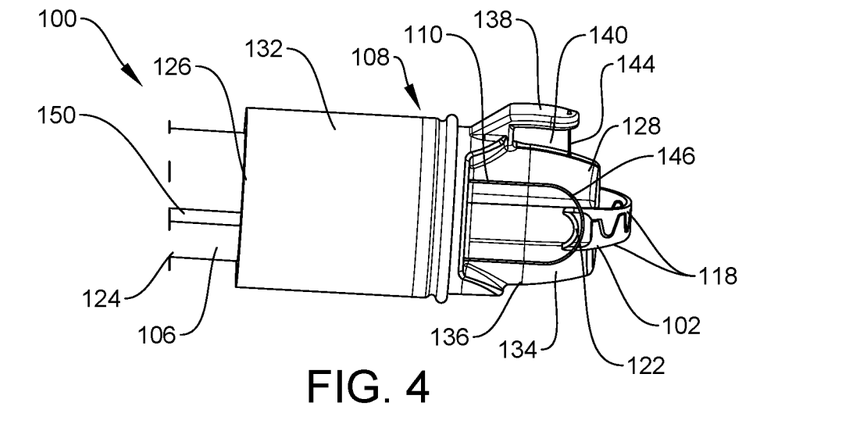
FIG. 4 shows another longitudinal side view of the distal portion of the system of FIG. 1, in an initial deployed configuration.
Figure 5:
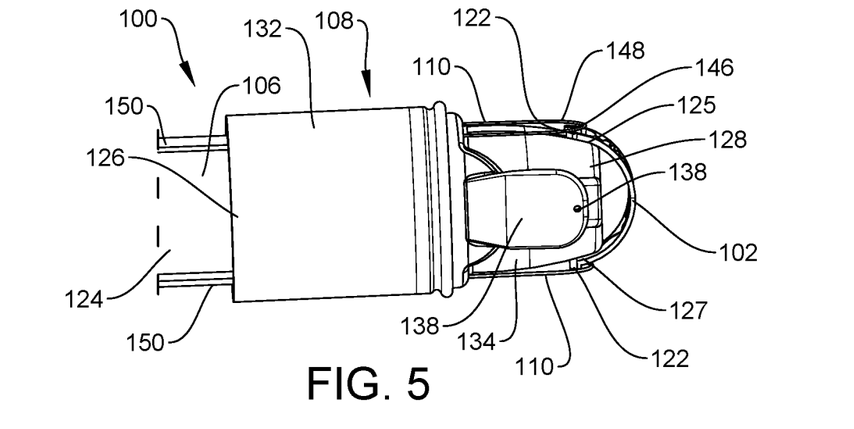
FIG. 5 shows another longitudinal side view of the distal portion of FIG. 4.

According to an exemplary method for tissue closure utilizing the clipping system 100, the clip 102 may be inserted through a body lumen such as, for example, the GI tract, to a target area within the body lumen via the endoscope 104. As described above, in the insertion configuration, as shown in FIG. 3, the clip 102 is mounted to the distal end 106 of the endoscopic shaft 124 via the adapter 108, so that the jaws 118 are separated from one another toward the open configuration. The clip 102 is guided to the target area via the endoscope 104, and positioned over a target tissue. A suction force may be applied through a working channel of the endoscope 104 so that the target tissue may be drawn into the channel 130 of the adapter 108. Thus, when the clip 102 is moved toward the initial deployed configuration via, for example, the first knob 162, jaws 118 of the clip 102 are permitted to revert to their biased closed configuration, as shown in FIGS. 4-5, so that the tissue suctioned into the channel 130 is gripped by the jaws 118 of the clip 102. In one embodiment, as described above, the clip 102 may be moved toward the initial deployed configuration by tensioning the deployment element 144 so that the deployment element 144 pushes distally against the clip 102. The clip 102 is thereby pushed distally off of the adapter 108 and is permitted to revert to its biased closed configuration.

Figure 6:
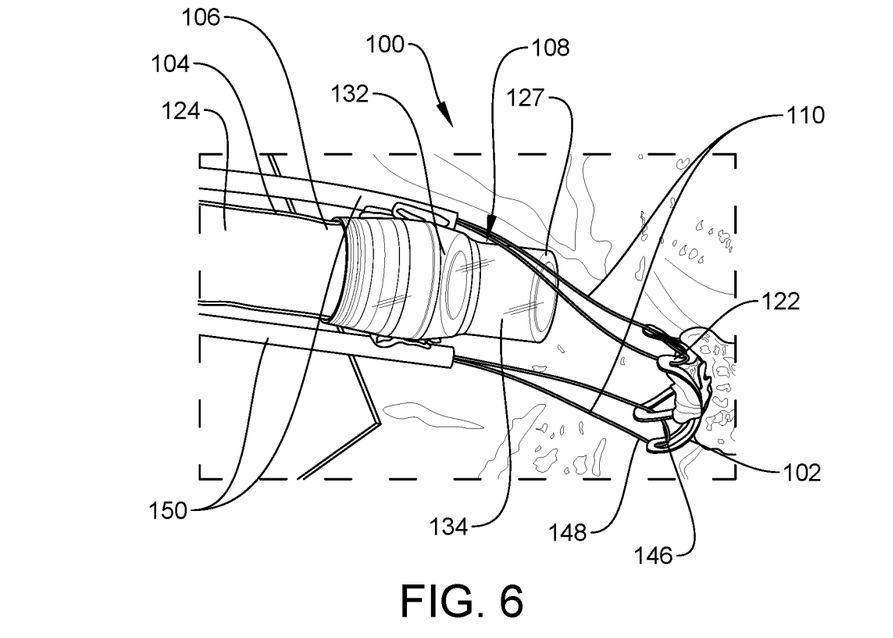
FIG. 6 shows a perspective view of the distal portion of the system of FIG. 1, in a review configuration.

It will be understood by those of skill in the art that suctioning and/or gripping of the tissue in this initial deployed configuration obstructs an imaging/optical lens of the endoscope 104 so that the user is unable to visualize and/or confirm whether a desired target tissue has been properly clipped. When the clip 102 is moved toward the review configuration, as shown in FIG. 6, however, the extending members 102 are moved distally relative to the endoscopic shaft 124 so that the clip 102 is moved away from the distal end 106 of the endoscopic shaft 124. In particular, extending the extending members 110 distally relative to the endoscopic shaft 124 via, for example, the second knob 164, allows the endoscope 104 to be drawn proximally away from the clip 102 while the clip 102 remains clipped on the tissue and the distal portion 134 of the adapter 108 is extended distally from the proximal portion of the adapter 108, creating distance between the clip 102 and the distal end 106 of the endoscopic shaft 124 selected so that the clip 102 may be visualized via the optical system of the endoscope 104.

If, upon visualization, the user determines that the clip 102 requires an adjustment and/or a repositioning relative to the target tissue, the extending members 110 may be translated proximally relative to the endoscope 104 until the clip 102 is moved proximally over the distal portion 134 of the adapter 108, as described above, toward the open configuration. The clip 102 may then be repositioned over the target tissue, as desired, and the clip 102 once again moved toward the initial deployed configuration, and then toward the review configuration. This process may be repeated, as necessary, until the user is able to visually confirm that the clip 102 has been clipped over the target tissue, as desired.

Once the user confirms that the target tissue has been clipped, as desired, the clip 102 may be moved from the review configuration to the final deployed configuration, as shown in FIG. 7, by releasing the clip 102 from the extending members 110. As described above, to release the clip 102, the extending members 110 are moved further distally relative to the endoscopic shaft 124. Since in the review configuration the clip 102 is clipped over the target tissue and thereby abuts against a tissue surface, moving the extending members 110 further distally causes the extending members 110 to also be moved distally relative to the clip 102. The extending members 110 are moved distally relative to the clip 102 until the distal ends 148 of the extending members 110 disengage the hinges 122 of the clip 102. According to one embodiment, the extending members 110 may be moved distally with respect to the clip 102 until the loops 146 at the distal end 148 disengage the hinges 122.

Once the loops 146 have been released from, for example, the C-shaped hinges 122, the distal ends 148 are permitted to revert to their biased configuration, moving radially away from one another. Thus, extending members 110, and the endoscope 104, may be withdrawn from the body so that just the clip 102 remains clipped over the target tissue.

It will be apparent to those skilled in the art that various modifications may be made in the present disclosure, without departing from the scope of the disclosure. Furthermore, those skilled in the art will understand that the features of any of the various embodiments may be combined in any manner that is not inconsistent with the description and/or the functionality of the embodiments.

What is claimed is:

1. A clipping system for treating tissue, comprising:
an adaptor extending longitudinally from a proximal end to a distal end, the adaptor configured to be mounted over a distal end of an insertion device;
a clip circumferentially mounted on the adapter and including first and second jaws, a first end of the first jaw being connected to a first end of the second jaw via a first hinge and a second end of the first jaw being connected to a second end of the second jaw via a second hinge so that the first and second jaws are movable between an insertion configuration, in which the first and second jaws are separated from one another to receive tissue therebetween and an initial deployed configuration in which the first and second jaws are drawn toward one another to grip tissue therebetween, at least one of the first and second hinges being biased to draw the clip toward the initial deployed configuration;
a deployment member configured to move the clip distally over and off of the adapter so that, as the clip leaves the adapter, the clip moves from the insertion configuration to the initial deployed configuration; and
a first extending member releasably coupled to the clip and movably connected to the adapter, the first extending member being configured to permit withdrawal of the adapter proximally away from the clip while the first extending member remains coupled to the clip to place the system in a review configuration in which the clip is physically separated from the adapter to enhance visual observation of the clip, the first extending member being operable to retract the clip proximally over the adapter so that the clip is forced open as the clip is retracted over the adapter freeing the clip from tissue on which it had been clipped.

2. The system of claim 1, wherein the first extending member is releasably coupled to the first hinge so that, when the clip is observed to be in a desired position, the clip can be finally deployed from the system by separating the first extending member from the clip.

3. The system of claim 2, further comprising a second extending member releasably coupled to the second hinge of the clip and movably connected to the adapter, the second extending member being configured to remain coupled to the clip while the system is moved to the review configuration, the second extending member being operable to cooperate with the first extending member to retract the clip proximally over the adapter from one of the review and initial deployment configurations.

4. The system of claim 2, wherein a distal end of the first extending member includes a loop configured to be hooked to the first hinge.

5. The system of claim 4, wherein the distal end of the first extending member is biased radially away from a longitudinal axis of the adapter so that, when the loop of the first extending member is released from the first hinge, the distal end of the first extending member springs laterally outward to disengage from the clip.

6. The system of claim 5, wherein the loop of the first extending member is configured to engage the clip so that a distally directed force applied to the first extending member is transmitted to the clip to move the clip distally over and off of the adapter, the loop of the first extending member being configured so that, when the clip applies a proximally directed force of at least a predetermined magnitude to the first extending member, the loop of the first extending member slides off of the first hinge to disengage the clip from the first extending member.

7. The system of claim 1, further comprising a user interface coupled to a proximal end of the deployment member and a proximal end of the first extending member to control a movement of the clip between the insertion configuration, the initial deployed configuration and the review configuration.

8. The system of claim 7, wherein the user interface includes a first knob connected to the proximal end of the deployment member and a second knob connected to the proximal end of the first extending member.

9. The system of claim 8, further comprising a first lumen extending proximally from the adapter to the user interface, the first extending member extending through the first lumen so that the first extending members is longitudinally movable relative to the first lumen.

10. The system of claim 1, wherein a distal portion of the adapter, over which the clip is configured to be mounted, includes a flat portion extending along an exterior surface thereof to reduce a friction between the clip and the adapter as the clip slides distally along the adapter toward a final deployed configuration.

11. A clipping system for treating tissue, comprising:
an endoscope including a shaft extending longitudinally from a proximal end to a distal end;
an adapter including a proximal portion mounted over the distal end of the shaft of the endoscope and a distal portion extending distally from the proximal portion;
a clip circumferentially mounted on the adapter and including first and second jaws, each of the pair of jaws extending along a curve from a first end to a second end, first ends of the pair of jaws connected to one another via a first hinge and second ends of the pair of jaws connected to one another via a second hinge so that the pair of jaws are movable between an open insertion configuration, in which the pair of jaws are separated from one another, and a closed configuration, in which the pair of jaws are moved toward one another;
a deployment member configured to move the clip distally relative to the adapter from the open insertion configuration to an initial deployed configuration by moving the clip distally off of the adapter so that the clip is moved toward the closed configuration; and
first and second extending members extending from proximal ends accessible to a user via a user interface at the proximal end of the shaft to distal ends releasably coupled to the clip, so that a distal movement of the first or second extending member relative to the endoscope moves the clip distally away from a distal end of the adapter from the initial deployed configuration to a review configuration by a distance selected so that the clip is visible via the endoscope.

12. The system of claim 11, wherein the first extending member is releasably coupled to the first hinge of the clip and the second extending member is releasably coupled to the second hinge of the clip.

13. The system of claim 12, wherein the distal ends of each of the first and second extending members are biased radially away from a longitudinal axis of the adapter so that, when the first and second extending member are coupled to the first and second hinges, the distal ends of the first and second extending members are restrained toward an engaging configuration, and, when the distal ends of the first and second extending members are disengaged from the first and second hinges, the distal ends of the first and second extending members revert to their biased configuration to release the clip therefrom in a final deployed configuration.

14. The system of claim 11, wherein the pair of jaws are biased toward the closed configuration so that, when the clip is circumferentially mounted over the adapter, an exterior surface of the adapter holds the pair of jaws toward the open insertion configuration and, when the clip is moved toward the initial deployed configuration, the pair of jaws are permitted to revert to the closed configuration.

15. The system of claim 11, further comprising first and second lumens extending proximally from the adapter to the user interface, each of the first and second extending members extending through a corresponding one of the first and second lumens so that the extending members are longitudinally movable relative to the first and second lumens, the first and second lumens extending along opposing sides of the shaft of the endoscope.

16. A method for treating tissue, comprising:
inserting a clip to a target area in a body lumen via an endoscope, the clip circumferentially mounted on an adaptor over a distal end of an endoscopic shaft, in an open insertion configuration in which jaws of the clip are separated from one another;
applying a suction force through a working channel of the endoscope so that tissue is drawn into a channel of the adapter and between the jaws of the clip;
moving the clip from the open insertion configuration to an initial deployed configuration by pushing the clip distally off of the adapter through a deployment member so that the jaws revert to a biased closed configuration, in which the jaws extend toward one another to grip the tissue received therebetween; and
moving extending members, distal ends of which are releasably coupled to the clip, distally relative to the endoscopic shaft so that the clip is moved distally away from a distal end of the adapter toward a review configuration in which the clip is visible via the endoscope.

17. The method of claim 16, further comprising reviewing the clip in the review configuration to determine whether a position of the clip relative a target tissue requires repositioning.

18. The method of claim 17, wherein, when it is determined that the clip requires repositioning, moving the extending members proximally relative to the endoscope until the clip is drawn proximally over the adaptor towards the open insertion configuration and repositioning the clip over the target tissue.

19. The method of claim 16, further comprising disengaging the extending members from the clip to release the clip in a final deployed configuration, in which the endoscope is removed from the body lumen.

20. The method of claim 19, wherein the distal ends of the extending members are biased radially outward relative to a longitudinal axis of the endoscopic shaft so that, when the extending members are disengaged from the clip, the distal ends of the extending members revert to their biased configuration so that the extending members are removable from the body lumen.

* * * * *